(12) United States Patent
Kunkel et al.

(10) Patent No.: US 9,842,583 B2
(45) Date of Patent: *Dec. 12, 2017

(54) ULTRASOUND PROBE WITH ACOUSTICAL LENS

(71) Applicant: KONINKLIJKE PHILIPS N.V., Eindhoven (NL)

(72) Inventors: Harry Amon Kunkel, Centre Hall, PA (US); Charles Clark Cruikshank, Belleville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 45 days.

This patent is subject to a terminal disclaimer.

(21) Appl. No.: 14/967,752

(22) Filed: Dec. 14, 2015

(65) Prior Publication Data

US 2016/0098984 A1    Apr. 7, 2016

Related U.S. Application Data

(63) Continuation of application No. 14/240,766, filed as application No. PCT/IB2012/054691 on Sep. 10, 2012, now Pat. No. 9,214,152.

(60) Provisional application No. 61/538,986, filed on Sep. 26, 2011.

(51) Int. Cl.
*G10K 11/30* (2006.01)
*A61B 8/00* (2006.01)
*G10K 11/18* (2006.01)
*A61B 8/08* (2006.01)

(52) U.S. Cl.
CPC ............ *G10K 11/30* (2013.01); *A61B 8/4272* (2013.01); *A61B 8/4444* (2013.01); *A61B 8/4483* (2013.01); *G10K 11/18* (2013.01); *A61B 8/5269* (2013.01)

(58) Field of Classification Search
CPC ...... G10K 11/18; G10K 11/30; A61B 8/4444; A61B 8/4483; A61B 8/5269; A61B 8/4272

See application file for complete search history.

(56) References Cited

U.S. PATENT DOCUMENTS

| | | | |
|---|---|---|---|
| 4,880,012 A | 11/1989 | Sato | |
| 5,371,717 A | 12/1994 | Bolorforosh | |
| 5,577,507 A | 11/1996 | Snyder et al. | |
| 7,719,170 B1 | 5/2010 | Kim et al. | |
| 9,214,152 B2 * | 12/2015 | Kunkel | A61B 8/4272 |
| 2005/0261590 A1 | 11/2005 | Ogawa et al. | |
| 2008/0189932 A1 | 8/2008 | Sliwa et al. | |
| 2011/0071396 A1 | 3/2011 | Sano et al. | |

(Continued)

FOREIGN PATENT DOCUMENTS

| | | | | |
|---|---|---|---|---|
| EP | 2289419 A1 | 3/2011 | | |
| NL | EP 2748813 A1 * | 7/2014 | ........... | A61B 8/4272 |

(Continued)

*Primary Examiner* — Daniel Pihulic

(57) ABSTRACT

The present invention relates to an ultrasound probe (60) comprising: an ultrasound transducer (12) having an emission surface (24) for generating ultrasound waves, and an acoustical lens (12) with a first part (64) having an inner surface (66) facing the emission surface (24), wherein the inner surface (64) comprises a plurality of protrusions (74) and/or recesses (76) for scattering reflections of ultrasound waves.

14 Claims, 5 Drawing Sheets

(56) References Cited

U.S. PATENT DOCUMENTS

| | | |
|---|---|---|
| 2012/0215138 A1 | 8/2012 | Zhong et al. |
| 2014/0204717 A1* | 7/2014 | Kunkel ................ A61B 8/4272 367/137 |
| 2016/0098984 A1* | 4/2016 | Kunkel ................ A61B 8/4272 367/137 |

FOREIGN PATENT DOCUMENTS

| | | | |
|---|---|---|---|
| WO | 2008051473 A2 | 5/2008 | |
| WO | 2008090504 A1 | 7/2008 | |
| WO | 2010086779 A2 | 8/2010 | |
| WO | WO 2013046080 A1 * | 4/2013 | ........... A61B 8/4272 |

* cited by examiner

ULTRASOUND PROBE WITH ACOUSTICAL LENS

This application claims the benefit or priority of and describes relationships between the following applications: wherein this application is a continuation of U.S. patent application Ser. No. 14/240,766, filed Sep. 10, 2012, which is the National Stage of International Application No. PCT/IB2012/054691, filed Sep. 10, 2012, which claims the priority of U.S. Provisional application 61/538,986 filed Sep. 26, 2011, all of which are incorporated herein in whole by reference.

FIELD OF THE INVENTION

The present invention relates to an ultrasound probe including an ultrasound transducer and an acoustical lens. The invention also relates to a part of an acoustical lens for an ultrasound probe.

BACKGROUND OF THE INVENTION

Ultrasound probes with acoustical lenses are often susceptible to fluid ingress. Typically, the acoustic stack within the lens is protected by an insulation layer of material which forms a moisture barrier to mitigate this problem. The insulation layer is often placed on an outer surface of the acoustical lens, where it is subject to wear, or directly on the acoustic stack itself where it can affect acoustical characteristics of the acoustic stack. The insulation layer can also be embedded within the acoustical lens itself so it is internal to a mechanically protected by the lens. A consequence of this arrangement is the introduction of an interface between the inner and outer portions of the acoustical lens which presents itself as a reflecting surface to ultrasound waves within the acoustical lens. Such an interface can give rise to unwanted reflections of ultrasound waves that may be of sufficient magnitude to be observable in the ultrasound image as artifacts, adversely affecting image quality. Therefore, it is desirable to design the interface which minimizes the magnitude and coherence of these reflections.

Ultrasound probes that employ acoustical lenses with multiple materials of different kind in two or more regions are also subject to the problem of internal interface reflections, since the boundaries between different materials are themselves reflecting surfaces capable of producing acoustic reflections which can lead to image artifacts. Choosing lens materials having specific acoustic properties has been common practice, e.g. for impedance matching purposes, but this restricts the number of lens materials suitable for use, and complicates the implementation of some of the technologies proposed in the references below.

WO 2010/086779 A2 describes a two-part fluid acoustical lens system with an interface between the fluids. Fluids with specific properties are chosen to reduce reflections only at certain incidence angles.

Other ultrasound probes with multiple acoustical lens systems have been proposed and each contains interfaces between acoustical lens materials and layers that present themselves as reflective surfaces.

U.S. Pat. No. 5,577,507 describes acoustical lens systems with an outer material of improved durability.

WO 2008/051473 A2 describes acoustical lens systems where materials are chosen to apodize or shape ultrasound beams to reduce sidelobes.

US 2011/0071396 A1 describes an acoustical lens with an internal electrical conducting surface for CMUT probes. None deal with the problem of internal acoustical lens reflections created in these structures.

SUMMARY OF THE INVENTION

It is an object of the present invention to provide an ultrasound probe with a robust solid body acoustical lens, wherein reflections of ultrasound waves arising from a reflecting surface within the acoustical lens are greatly reduced. A key feature of the current invention is the use of acoustic scattering to reduce the magnitude and coherency of acoustic reflections from the reflecting surface.

In a first aspect of the present invention an ultrasound probe is presented, including an ultrasound transducer having an emission surface for generating ultrasound waves, and an acoustical lens with a first part having an inner surface facing the emission surface, wherein the inner surface comprises a plurality of protrusions and/or recesses for scattering reflections of ultrasound waves.

In a further aspect of the present invention a part of an acoustical lens for an ultrasound probe is presented, including an inner surface for facing an emission surface of an ultrasound transducer, wherein the inner surface comprises a plurality of protrusions and/or recesses for scattering reflections of ultrasound waves.

The invention is based on the idea that a reflecting surface within an ultrasound probe can be designed in a way that reflections from the surface are scattered throughout different spatial directions. This is depending on where they strike the reflecting surface. These reflections are delayed by various times depending on the region in which they will stray. As a result, reflected parts of ultrasound waves arrive at different times at a sensor or the emission surface. This is reducing the coherence of the reflections received across the surface, thereby reducing the response of the transducer to these reflections since transducer elements respond most strongly to ultrasound waves which are coherent across a sensor surface. Additionally, cancellation of reflected parts of ultrasound waves is achieved by shifted phases of the reflected parts, and an overall magnitude of the backscattered reflection is reduced by virtue of destructive interference. These two effects are very effective at reducing the transducer's response to waves reflecting from the reflecting surface, respectively interface, and artifacts are reduced accordingly. Scattering ultrasound waves is made possible by using irregular non-planar interface geometry to reduce the magnitude and coherence of acoustic reflections from interfaces and the inner surface or inner surfaces, interior to the acoustical lens. In other words, the basic idea is to use an uneven and rough inner surface The ultrasound transducer comprises at least one ultrasound transmitter element, e.g. a piezoelectric element. It is preferred if the ultrasound transducer comprises an array of ultrasound transmitter elements.

Preferred embodiments of the invention are defined in the dependent claims.

In an embodiment the acoustical lens includes an insulation layer covering at least a part of the inner surface. In this embodiment an insulation layer is provided for protecting the ultrasound probe from fluid ingress. Such layers are typically very thin. They can, for example, be evaporated onto the inner surface of the first part. Hence, the insulation layer will also form a surface maintaining the profile of the protrusions and/or recesses for scattering reflections of ultrasound waves. Since such insulation layers are often very reflective to ultrasound waves, it is advantageous that scattering characteristics caused by the protrusions and/or recesses from the first part are passed on to the insulation layer, wherein reflections caused by the insulation layer are effectively scattered.

In a further embodiment the acoustical lens includes a coupling layer for coupling the insulation layer and the first part with the ultrasound transducer. In this embodiment an additional layer of material is provided between the insulation layer and the ultrasound transducer. In a preferred embodiment the ultrasound probe is produced by the following steps: First the first part, for example a lens cap is provided and its inner surface is covered with the insulation layer. Then the first part is arranged in a correct position and orientation to the ultrasound transducer, wherein a small gap between the first part and the transducer is provided. Finally, the coupling layer is provided by injecting a fluid or viscous material between the first part and the ultrasound transducer filling out the gap and recesses. The fluid or viscous material is then hardening so as to provide a sufficient bond between the first part, the insulation layer and the ultrasound transducer. For example, the coupling layer can be made of fluid room temperature vulcanizing silicone rubber. Hence, very good mechanically and acoustically coupling between the ultrasound transducer and the first part is achieved. In that, an insulation layer is gained which is arranged within the acoustical lens. The acoustical lens preferably incorporates the first part, the insulation layer and the coupling layer.

Further, using materials with different acoustical characteristics for the first part and the coupling layer can lead to a reflecting inner surface. In this case, the invention reduces reflections of the inner surface. As an advantageous effect the usage of materials with different acoustical characteristics for the first part and the coupling layer is made possible without a loss of measurement quality.

In a further embodiment the protrusions and/or recesses are forming a periodic progression in a cross-sectional view of the inner surface. In this embodiment the protrusions and/or recesses take the form of a periodic progression along the inner surface. The usage of the periodic progression leads to the advantage that its period and amplitude can be easily adapted to wavelengths of the ultrasound waves generated by the ultrasound transducer as to provide optimal scattering characteristics. Additionally, these protrusions and/or recesses can be easily produced on different sizes of inner surfaces. It is conceivable that a plurality of periodic progressions is progressing simultaneously in different cross-sectional views of different spatial directions. Hence, a plurality of three dimensional distortions for scattering reflections of ultrasound waves in different spatial directions is provided.

In a further embodiment the protrusions and/or recesses are forming an aperiodic progression in a cross-sectional view of the inner surface. In this embodiment the protrusions and/or recesses take the form of an aperiodic progression along the inner surface. The usage of the aperiodic progression leads to the advantage that a change in period and amplitude can be adapted to different wavelengths of the ultrasound waves generated by the ultrasound transducer in different regions of the first part as to further enhance scattering characteristics. It is conceivable that a plurality of aperiodic progressions is progressing simultaneously in different cross-sectional views of different spatial directions. It is also conceivable to combine periodic and aperiodic progressions in different spatial directions. Hence, a plurality of three dimensional distortions with defined different sizes for scattering reflections of ultrasound waves in different spatial directions is provided.

In a further embodiment the protrusions and/or recesses are forming an irregular progression in a cross-sectional view of the inner surface. In this embodiment the protrusions and/or recesses take the form of a progression along the inner surface with an irregular structure, e.g. a random structure. The orientation, spacing and/or size of the protrusions and/or recesses can therefore vary within the progression. It is conceivable to provide a general roughness with the inner surface in this case. The general roughness is preferably on a level greater than an eighth of the wavelength of the reflected ultrasound wave. Hence, a very effective scattering is achieved with very high manufacturing advantages.

In a further embodiment at least one protrusion and/or recess of the plurality of protrusions and/or recesses has a triangular structure in a cross-sectional view of the inner surface. In this embodiment at least one of the protrusions and/or recesses are designed as to have sharp edges and flat flanks. It is preferred if the triangular structure is used in addition to a periodic progression, wherein the periodic progression would form a triangular progression. This kind of structure can be produced very easily and scatters the ultrasound waves very effectively. Additionally in this case, an insulation layer can be easily evaporated with a constant thickness onto the inner surface.

In a further embodiment the at least one protrusion and/or recess of the plurality of protrusions and/or recesses has a pyramidal structure. In this embodiment at least one pyramidal spatial structure is intended in or at the inner surface for scattering the reflections of ultrasound waves. Hence, in this embodiment the reflected ultrasound waves are scattered in more than two spatial dimensions. Hence, the effectiveness of the scattering is further enhanced since the reflections are dispersed across a sensor surface or the surface of the ultrasound transducer in additional spatial directions.

In a further embodiment at least one protrusion and/or recess of the plurality of protrusions and/or recesses has a height of approximately 100 μm. In this embodiment a recess is extending approximately 100 μm in its height. This is corresponding to odd multiples of acoustic wavelength λ at frequencies of interest, e.g. in the silicone rubber lens materials. This height refers to the distance between the highest and the lowest point of the inner surface, seen in direction of ultrasound waves traveling normal to the inner surface. This specific dimension is very advantageous for frequencies typically used within ultrasound transducer technology, since 100 μm corresponds to about ¾λ at an ultrasound frequency of 7.5 MHz and ¼λ at an ultrasound frequency of 2.5 MHz. This is spanning the range of frequencies typically used in medical ultrasound imaging. When other lens materials and frequencies are used, it is often desirable to choose heights that correspond to odd multiples of acoustic wavelength. It is preferred to use heights above 50 μm. Experiments of the applicant have shown that this height leads to a very effective scattering of reflected ultrasound waves.

In a further embodiment at least a part of the inner surface is tilted in space with respect to the emission surface. In this embodiment the inner surface is arranged non-parallel to the emission surface. It is preferred, if the tilting between the emission surface and the inner surface is made with reference to an average surface height of the inner surface. By tilting the inner surface with respect to the emission surface reflections of ultrasound waves emitted from a specific area of the ultrasound transducer can be scattered in a collective main direction. This is especially advantageous, if an array of transmitter elements is used as an ultrasound transducer.

In this case at least parts of the inner surface can be tilted to the emission surface of a specific transmitter element as to scatter the reflections away from this specific transmitter element onto another transmitter element of the array. Hence, the tilting can be made in general or partially with respect to the array and provides an enhancement of efficiency regarding the scattering of the ultrasound waves.

In a further embodiment the first part is made of silicone rubber. In this embodiment the first part is made of a specific material leading to a very cost-effective first part. Additionally, the protrusions and/or recesses can be produced very easily and cost-effectively, e.g. by injection molding methods.

In a further embodiment the insulation layer is made of parylene. In this embodiment the insulation layer is made of a specific material leading to a very effective protection of the ultrasound probe against fluid ingress. Further, parylene is a material, which can be applied in a very thin layer, e.g. 13 μm, wherein the scattering characteristic of the protrusions and/or recesses is preserved. Hence, a very effective moist barrier can be used without a decrease in measurement quality.

In a further embodiment the coupling layers are made of silicone rubber. By using silicone rubber for the coupling layer, injection molding techniques can be used as to bond the first part with the insulation layer and the ultrasound transducer. As an advantage, injecting fluid silicone rubber leads to a coupling layer avoiding the appearance of air pockets within the acoustical lens very efficiently also within the uneven inner surface. This is advantageous, since air pockets would lead to additional reflections of ultrasound waves.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
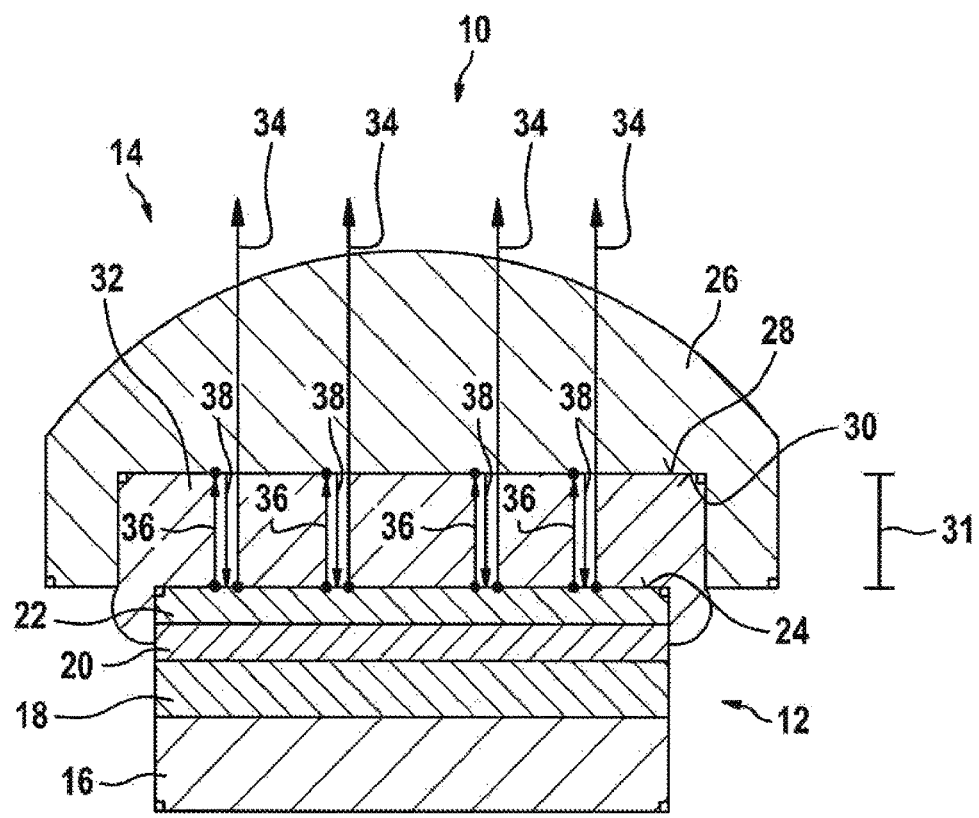
FIG. 1 shows a cross-section along the short axis of an ultrasound probe with an acoustical lens having a first part with a flat inner surface.

FIG. 1 shows schematically an ultrasound probe 10, comprising an ultrasound transducer 12 and an acoustical lens 14. The ultrasound probe 10 in FIG. 1 is shown in a cross-sectional view and is an example for explaining reflections of ultrasound waves within the acoustical lens.

The ultrasound transducer 12 comprises four layers. It comprises a backing layer 16, a piezoelectric layer 18 and two matching layers 20 and 22. All those layers are bonded together as to form the combined ultrasound transducer 12. The ultrasound transducer 12 has an emission surface 24, which is a surface of the matching layer 22 facing in direction of the acoustical lens 14. In use, the piezoelectric layer 18 is vibrating at a specified driving frequency and is generating ultrasound waves.

The acoustical lens 14 comprises a first part 26 formed as a lens cap made of silicone rubber. As shown in the cross-sectional view, the first part 26 comprises an inner surface 28 facing the ultrasound transducer 12, in particular the emission surface 24. FIG. 1 has to be understood in a way that the inner surface 28 and the emission surface 24 are both two-dimensional planes which expand orthogonally from the paper plane. Thereby, both surfaces 24 and 28 are arranged in parallel to each other.

The inner surface 28 is covered entirely with a thin insulation layer 30. The insulation layer 30 is made of parylene, or some other polymer leading to a protection of the ultrasound transducer 12 with respect to moisture. For manufacturing the ultrasound probe 10, the first part 26 is arranged with respect to the ultrasound transducer 12 as shown. The inner surface 28 is already covered with the insulation layer 30 at this point. The inner surface 28 and the emission surface 24 are arranged in a way that both expand in parallel to each other. Additionally, a distance 31—a stand-off—between the insulation layer 30 and the ultrasound transducer is maintained. Accordingly, a gap is created between the first part 26 and the ultrasound transducer 12. As to accomplish the ultrasound probe 10, fluid room temperature vulcanizing silicone rubber is injected into the gap as to form the coupling layer 32. Finally, the fluid room temperature vulcanizing silicone rubber is hardened.

In use the ultrasound transducer 12 generates ultrasound waves which are transmitted through the acoustical lens 14. This is schematically illustrated by arrows 34. The contact planes of the insulation layer 30 are reflecting the ultrasound wave at least partially. Parts of the ultrasound waves are sent to the insulation layer 30 in direction of the arrows 36. At the insulation layer 30 these parts are reflected and sent back via the arrows 38. The arrows 34, 36 and 38 are exemplarily shown with distances between each other for illustrative purposes only. It has to be understood that the arrows 34, 36 and 38 are actually expanding through the same part of space in reality.

As shown in FIG. 1, all arrows 36 are of the same length, since the distance between the emission surface 24 and the insulation surface 30 is constant for the whole emission surface 24. Accordingly, all arrows 38 are of the same length. Therefore, the reflected parts of the ultrasound waves are arriving at the ultrasound transducer 12 at the same time. Hence, a combined impulse is generated by the cumulated force of those reflected parts of the ultrasound waves. This combined impulsive force leads to artifacts affecting measurement quality. Therefore, it leads to artifacts in the image.

Figure 2:
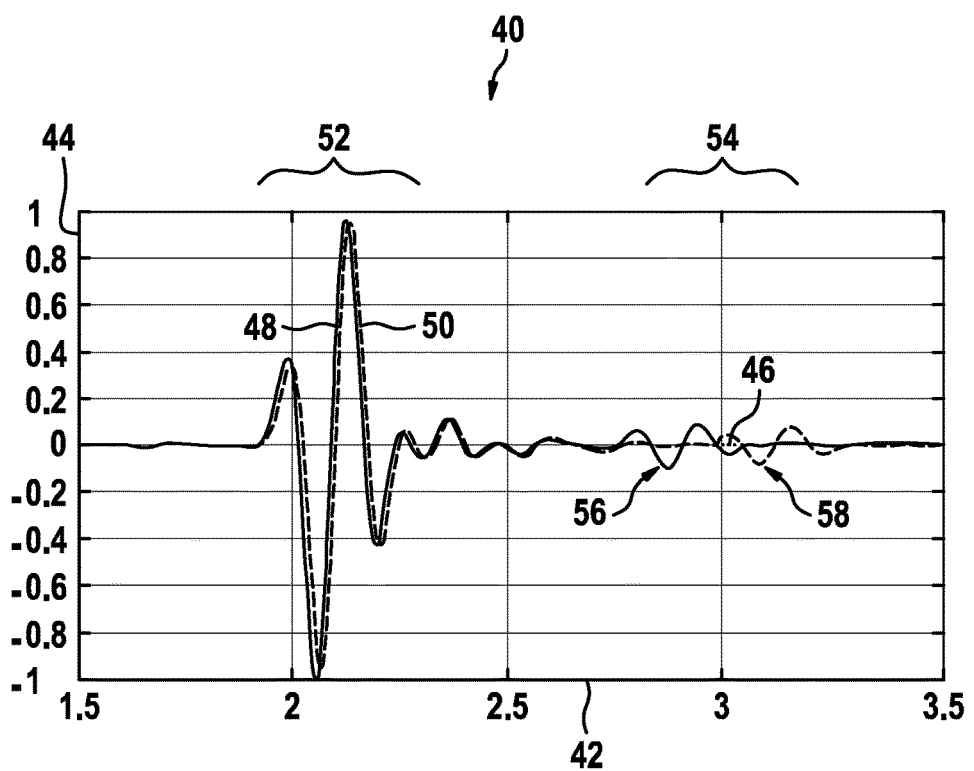
FIG. 2 shows a diagram of transmit impulse responses calculated with and without the use irregular inner surfaces.

FIG. 2 shows a diagram 40 comprising an abscissa 42 and an ordinate 44. The abscissa 42 refers to time, wherein the unit is milliseconds. The ordinate 44 refers to a voltage of the ultrasound transducer 12. Within the diagram 40, three curves 46, 48 and 50 are shown.

Curve 46 is an impulse response of ultrasound probe similar to the ultrasound probe shown in FIG. 1 but without the insulation layer 30. As shown in an interval 52, the ultrasound transducer 12 is stimulated as to transmit an ultrasound wave. In a further interval 54, at a time where a reflection from the inner surface 28 might be expected, none is observed since no insulation layer 30 is present.

Curve 48 is an impulse response of the ultrasound probe 10 shown in FIG. 1 with the insulation layer 30 present and positioned at the standoff 31. The transducer 12 is driven in the interval 52 in a similar way as shown with respect to curve 46. However, in interval 54 a reflection artifact 56 arises, caused by the reflection of ultrasound waves from the insulation layer 30. The magnitude of this reflection artifact would be sufficient enough to adversely affect the image.

Curve 50 is an impulse response of an ultrasound probe shown in FIG. 1 with the insulation layer 30 positioned at a standoff 31 larger than that in the preceding example. As shown in interval 52, approximately the same driving signal is used for this ultrasound probe. Based on the larger standoff 31 an reflection artifact 58 is generated which is delayed in time relative to the reflection artifact 56 because the pathlength of the ultrasound wave is longer due to the increased standoff 31. However, it can be observed from FIG. 2 that substantially the same kind of impulse similar in frequency and amplitude is reflected. Furthermore, FIG. 2 demonstrates that the delay of a reflection artifact in interval 54 is proportional to standoff 31, so that an inner surface 28 with variable standoffs 31 would produce reflection artifacts of variable delays.

Figure 3:
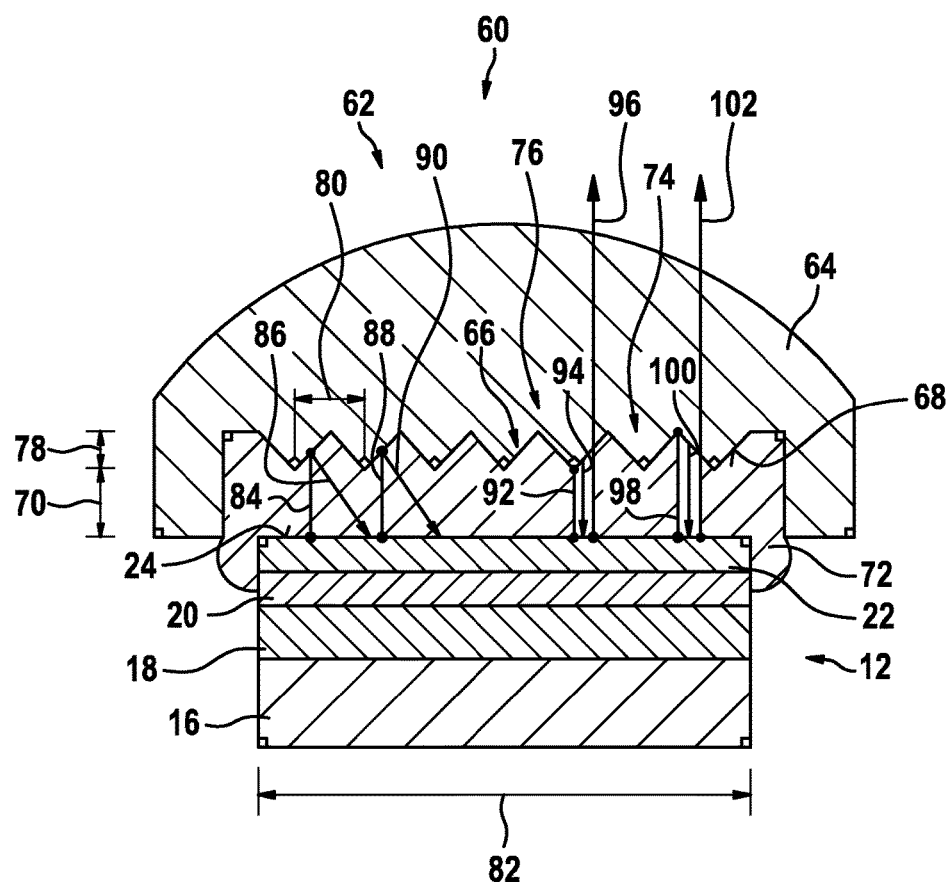
FIG. 3 shows a cross-section along the short axis a first embodiment of an ultrasound probe according to the invention.

FIG. 3 shows schematically an ultrasound probe 60 according to the invention. The ultrasound probe 60 in FIG. 3 is shown in a cross-sectional view. The same components as described with respect to the ultrasound probe 10 in FIG. 1 are referred to with the same reference signs. The ultrasound probe 60 comprises an acoustical lens 62. The ultrasound lens 62 has a first part 64 forming an outer lens cap. The first part 64 has an inner surface 66 which is covered with an insulation layer 68. Between the inner surface 66 and the ultrasound transducer 12 a stand-off 70 is present in which a coupling layer 72 is arranged. The first part 64, the insulation layer 68 and the coupling layer 72 are of the same materials as the first part 26, the insulation layer 30 and the coupling layer 32 shown in FIG. 1.

In contrast to the inner surface 28 of FIG. 1, the inner surface 66 comprises a plurality of protrusions 74 and recesses 76. In FIG. 3 only one protrusion 74 and one recess 76 have been referenced to with reference signs exemplarily. The transducer 12 is placed at a standoff 70 relative to the first part 64. This distance is measured from the most upper surface of the transducer 12 to the nearest surface points of the inner surface 66, in particular, the peaks of the protrusions 74. An insulation layer 68 conforms to the inner surface 66. As shown, a height from the highest points of the inner surface 66 to its lowest points is described by the height 78 which is approximately 100 μm in this example. The distance 80 between protrusions and the elevation aperture 82 varies according to the type of ultrasound transducer being designed.

The protrusions 74 and recesses 76 form a periodic progression of a triangular structure in this cross-sectional view. This leads to a scattering of reflected parts of the ultrasound waves in a way that within each period of the periodic progression the reflected parts are scattered into different spatial directions. Accordingly, the reflected parts travel back to the transducer 12 across different distances. Therefore, for each period of the progression the reflected parts of the ultrasound waves are distributed differently over time and space.

In particular, as shown with respect to arrow 84, a part of an ultrasound wave is traveling to the insulation layer 68. At the insulation layer 68 this part of the ultrasound wave is reflected into a direction 86 back to the transducer 12. At the same time at another point of the transducer 12 another part of the ultrasound wave is transmitted into a direction of an arrow 88. This part of the ultrasound wave is reflected at a further point of the insulation layer 68 which is slightly more distant to the transducer 12 and is traveling back in a direction according to arrow 90. Hence, the way to the reflecting insulation layer 68 and from the reflecting insulation layer 68 back to the ultrasound transducer 12 is longer than the way described with respect to the arrows 84 and 86. Hence, the part of the ultrasound wave reflected back in direction of the arrow 90 is traveling longer than the other part of the ultrasound wave. In that, scattering of the reflected parts of the ultrasound wave is achieved. Additionally, the different distances are leading to phase shifts between the reflected parts, wherein cancellation effects are provided as to further decrease a resulting impulse of the reflections.

Additionally, at the peak points of the protrusion 74 and the recesses 76 a direct reflection is generated. As shown with respect to arrow 92, this part of the ultrasound wave emitted from the transducer 12 is being reflected at a peak point of a protrusion 74 and therefore reflected back in the direction shown by the arrow 93. Additionally, an arrow 96 is shown which describes the traveling direction of this part of the ultrasound wave through the whole acoustical lens 62.

In the same way a further part of the ultrasound wave is traveling in direction of an arrow 98 to a peak point of a recess 76. This part of the ultrasound wave is reflected accordingly into direction of an arrow 100. Additionally, the traveling direction of the ultrasound wave is shown by a further arrow 102. As shown, the traveling ways for these parts of the ultrasound waves are differentiating in their length. Therefore, scattering of the reflected parts of the ultrasound waves is also given at these points.

For the sake of completeness it is stated that the arrows 92, 94 and 96 are actually expanding through the same parts in space but are shown next to each other for a better visualization. The arrows 98, 100 and 102 are arranged in the same way for the same reasons.

While the diagram in FIG. 3 shows a periodic structure of period 80, it is possible to use other structures for benefits of the wave scattering mechanisms described above to accrue. Aperiodic structures with a distance 80 that changes across the dimension of transducer 12 may be used. Similarly, shapes other than those strictly triangular may be used, but the triangular structure has proven to be quite effective.

Figure 4:
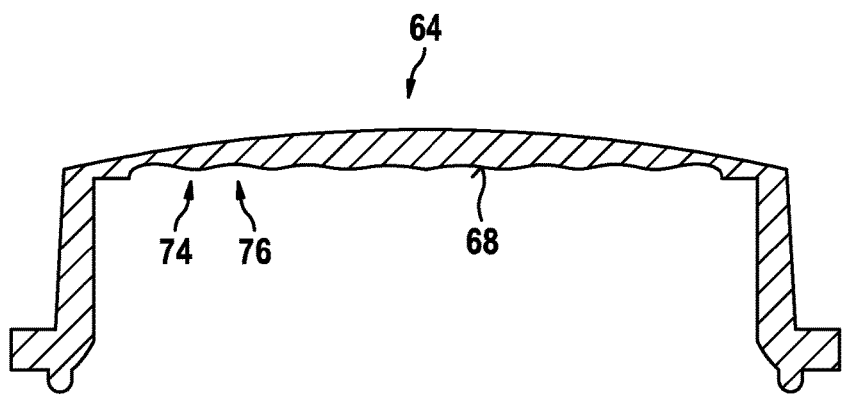
FIG. 4 shows a first embodiment of a first part according to the invention.

FIG. 4 shows a cross-sectional view of the first part 64 of FIG. 3 and its inner surface with an uneven structure in scale. As shown, the height of the recesses 76 and protrusions 76 are relatively small compared to the extension of the whole inner surface 68.

Figure 5:
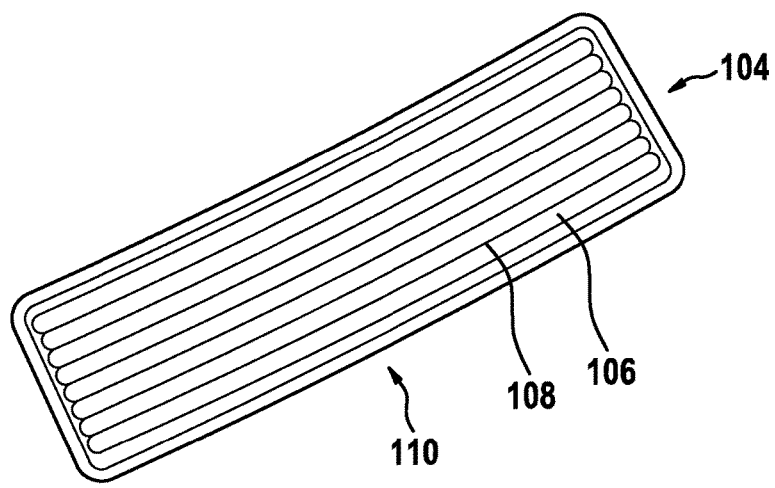
FIG. 5 shows a second view of the first part according to the invention.

FIG. 5 shows an isometric view of a further first part 104 which is adapted to fit to a curved linear array of ultrasound transmitter elements. Recesses 106 and protrusions 108 are expanding in a way as to cover the whole inner surface 110 continuously.

Figure 6:
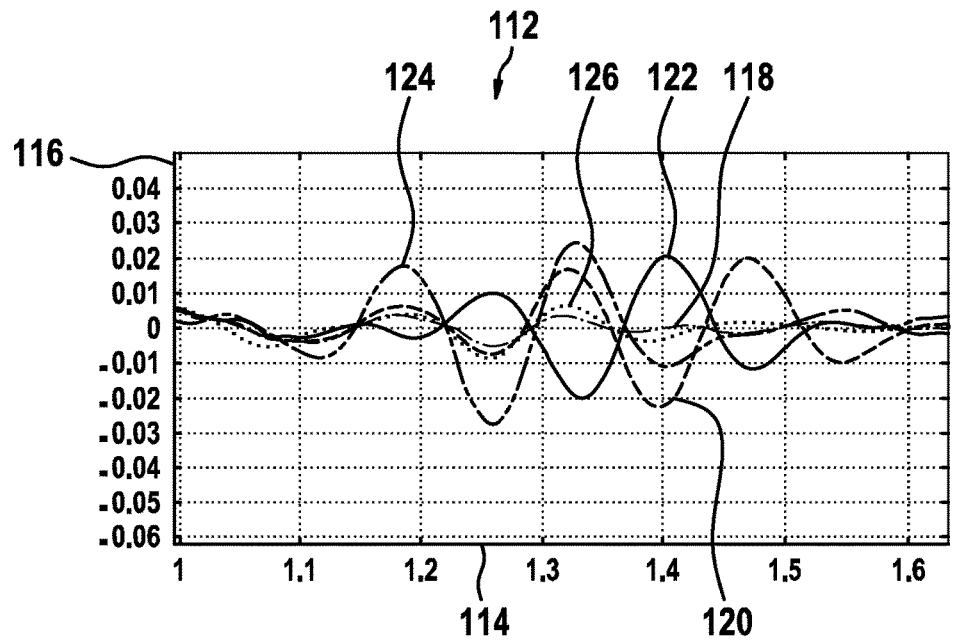
FIG. 6 shows a diagram of pulses reflected from inner surfaces of various protrusions, and the resulting destructive interference that results when these pulses are summed coherently across the face of the transducer.

FIG. 6 shows a further diagram 112 with an abscissa 114 referring to time in milliseconds and an ordinate 116 referring to a voltage of the piezoelectric element 20.

Within the diagram 112 five curves 118, 120, 122, 124 and 126 are shown. The Curves 120, 122, 124 and 126 represent calculated reflections of ultrasound waves from the insulation layer 68 located at four different distances from the transducer 12. These distances range from the distance 92 from the transducer to the peak protrusion of the inner surface 66, to the distance 98 from the transducer 12 to the farthest recess 76 of the inner surface 66. It can be seen from the diagram that these curves 120, 122, 124 and 126 are distributed over time. When each curve 120, 122, 124 and 126 is considered individually, the reflection it represents has a large magnitude which on its own would lead to reflection artifacts. When the curves 120, 122, 124 and 126 are coherently summed, like they are on an inner surface of continuously varying standoffs, the curve 118 results. Because the transducer 12 responds to the coherent sum of ultrasound waves impinging on its surface 24, the transducer 12 response will be proportional to curve 118 when receiving the reflections represented by the other curves 120, 122, 124 and 126 in the diagram. This demonstrates the effectiveness of using an irregular surface to phase shift reflections thereby reducing the effects of reflections.

Figure 7:
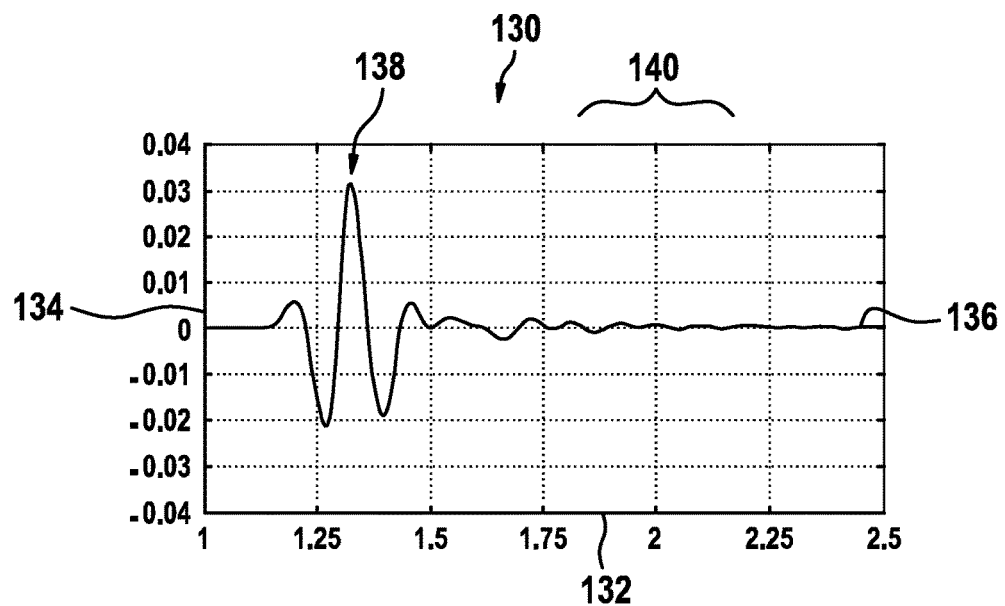
FIG. 7 shows a diagram describing a measure transmit response of an ultrasound probe according to the invention.

FIG. 7 shows a diagram 130 comprising an abscissa 132 for time in milliseconds and an ordinate 134 for a voltage at the piezoelectric layer 20. Within the diagram, a curve 136 is shown for the ultrasound probe 60 of FIG. 3. It shows an impulse response from an actual 6.5 MHz ultrasound probe 60 with a linear array and a grooved silicone rubber lens cap as the first part 64. The inner surface 66 is coated with the parylene insulation layer 68. While the usage of a lens cap with a flat inner surface, as shown in FIG. 1, would lead to a reflection artifact between 0.75 and 1.0 µs after a main excitation 138, the impulse response of the actual linear array shows no such reflection artifact. Therefore, an ultrasound probe is gained with reduced artifacts to reflections of ultrasound waves within an acoustical lens, and image quality is enhanced by using the invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An ultrasound probe comprising:
    an ultrasound transducer having an emission surface for generating ultrasound waves; and
    an acoustical lens comprising a first part having an inner surface facing the emission surface and a coupling layer between the inner surface and the emission surface, wherein the inner surface comprises a plurality of protrusions and/or recesses opposing the emission surface of the ultrasound transducer.

2. The ultrasound probe of claim 1, wherein the transducer comprises an array of ultrasound transmitter elements.

3. The ultrasound probe of claim 1, wherein the acoustical lens further comprises an insulation layer located between the inner surface and the emission surface.

4. The ultrasound probe of claim 1, wherein the coupling layer comprises different acoustical characteristics than the first part.

5. The ultrasound probe of claim 1, wherein at least a part of the inner surface is tilted in space with respect to the emission surface.

6. The ultrasound probe of claim 5, wherein the transducer comprises an array of ultrasound transmitter elements and the part of the inner surface is tilted to the emission surface of a first transmitter element so as to scatter the reflections away from the first transmitter element onto a second transmitter element of the array.

7. The ultrasound probe as claimed in claim 1, wherein the protrusions and/or recesses are aperiodic or periodic.

8. The ultrasound probe of claim 1, wherein the protrusions and/or recesses are aperiodic and a distance between the protrusions changes over a dimension of the transducer.

9. The ultrasound probe of claim 1, wherein protrusions and/or recesses of the inner surface form an undulating pattern.

10. The ultrasound probe of claim 1, wherein at least a part of the inner surface is parallel to the emission surface.

11. The ultrasound probe of claim 1, wherein the first part comprises silicone rubber.

12. The ultrasound probe of claim 3, wherein the insulation layer comprises parylene.

13. The ultrasound probe of claim 1, wherein the coupling layer comprises silicone rubber.

14. The ultrasound probe of claim 1, wherein the protrusions and/or recesses are periodic and a distance between the protrusions is the same over a dimension of the transducer.

* * * * *